(12) United States Patent
Schaller

(10) Patent No.: US 9,316,644 B2
(45) Date of Patent: Apr. 19, 2016

(54) METHOD FOR ESTABLISHING THE SENSITIVITY OF TUMOURS TO CAPECITABIN AND TEST KIT

(75) Inventor: Gerhard Schaller, Berlin (DE)

(73) Assignee: SANOXSYS GMBH, Munich (DE)

( * ) Notice: Subject to any disclaimer, the term of this patent is extended or adjusted under 35 U.S.C. 154(b) by 959 days.

(21) Appl. No.: 12/375,616

(22) PCT Filed: Aug. 1, 2007

(86) PCT No.: PCT/DE2007/001369
§ 371 (c)(1),
(2), (4) Date: Jun. 3, 2009

(87) PCT Pub. No.: WO2008/014779
PCT Pub. Date: Feb. 7, 2008

(65) Prior Publication Data
US 2009/0263399 A1    Oct. 22, 2009

(30) Foreign Application Priority Data

Aug. 2, 2006 (DE) .......................... 10 2006 037 158

(51) Int. Cl.
*A61K 31/00* (2006.01)
*G01N 33/574* (2006.01)

(52) U.S. Cl.
CPC ........ *G01N 33/57415* (2013.01); *G01N 33/574* (2013.01); *G01N 33/57419* (2013.01); *G01N 2333/52* (2013.01); *G01N 2333/71* (2013.01); *G01N 2333/90245* (2013.01); *G01N 2333/91142* (2013.01)

(58) Field of Classification Search
USPC ............... 424/141, 144, 489, 141.1; 514/700, 514/13.3; 435/7.23, 6.14
See application file for complete search history.

(56) References Cited

U.S. PATENT DOCUMENTS

2005/0281883 A1* 12/2005 Daniloff et al. ............... 424/489

OTHER PUBLICATIONS

Han et al., J Clin Pathol 2005; 58:650-654.*
Lin et al., Oncology (Williston Park). Dec. 2002; 16 (12 Suppl No. 14):31-7.*
Biganzoli et al., The Oncologist 2002; 7 (suppl 6):29-35.*
Tockman et al (Cancer Res., 1992, 52:2711s-2718s).*
Pritzker (Clinical Chemistry, 2002, 48:1147-1150).*
Busken, C et al. (Digestive Disease Week Abstracts and Itinerary Planner, 2003, abstract No. 850).*
Kaiser (Science, 2006, 313: 1370).*
Carter, S. K. et al. (Chemotherapy of Cancer; Second edition; John Wiley & Sons: New York, 1981; appendix C).*
Krontiris and Capizzi (Internal Medicine, 4th Edition, Editor-in-chief Jay Stein, Elsevier Science, 1994 Chapters 71-72, pp. 699-729).*
Taber's Cyclopedic Medical Dictionary (1985, F.A. Davis Company, Philadelphia, p. 274).*
Bowie et al (Science, 1990, 257:1306-1310).*
Rudikoff et al. (PNAS, USA, 1982, 79: 1979-1983).*
Coleman et al. (Research in Immunology, 1994; 145(1): 33-36).*
Abaza et al. (Journal of Protein Chemistry, vol. 11, No. 5, 1992.*
Burgess et al (J. of Cell Bio. 111:2129-2138, 1990).*
Steward [J. clin. Path., 32, Suppl. (Roy. Coll. Path.), 13, 120-125].*
Blanquicett et al. (Clin. Cancer Res., 2005, 11: 8773-8781).*
Twelves et al. (The Oncologist, 2001, 6: 35-39).*
Biganzoli et al. (The Oncologist, 2002, 7: 29-35).*
Bremnes et al. (Lung Cancer, 51: 143-158, Epub Dec. 19, 2005).*
PubMed abstract Bremnes et al.*
Tominaga, et al., Prognostic and Predictive Value of Thymidine Phosphorylase Activity in Early-Stage Breast Cancer Patients (Abstract), 2002, Clin. Breast Cancer 3 (1): 55.
Layman, Neoadjuvant Docetaxel and Capecitabine and the Use of Thymidine Phosphorylase as a Predictive Biomarker in Breast Cancer (Abstract), 2007, Clin Cancer Research, 13 (14): 4092.
Almhanna, et al., Association Between COX-2 Expression and Effectiveness of COX-2 Inhibitors in a Phase II Trial in Patients with Metastatic Colorectal Adenocarcinoma (Abstract) 2012, Anticancer Res 32(8): 3559.
Banerjee, et al., Mechanism of Disease: angiogenesis and the management of breast cancer, 2007, Nat Clin Pract Ocol 4 (9): 536.

* cited by examiner

*Primary Examiner* — Yan Xiao
(74) *Attorney, Agent, or Firm* — Buchanan Ingersoll & Rooney PC

(57) ABSTRACT

The invention relates to a method for establishing the sensitivity of tumors towards capecitabine, if applicable in combination with Docetaxel or Paclitaxel or the humanized antibody Herceptin, or COX-2 inhibitors or angiogenesis inhibitors and test kit.

Fields of application of the invention are the pharmaceutical industry and bio-sciences: biology, biochemistry, biotechnology, medicine and medicinal technology.

15 Claims, 1 Drawing Sheet

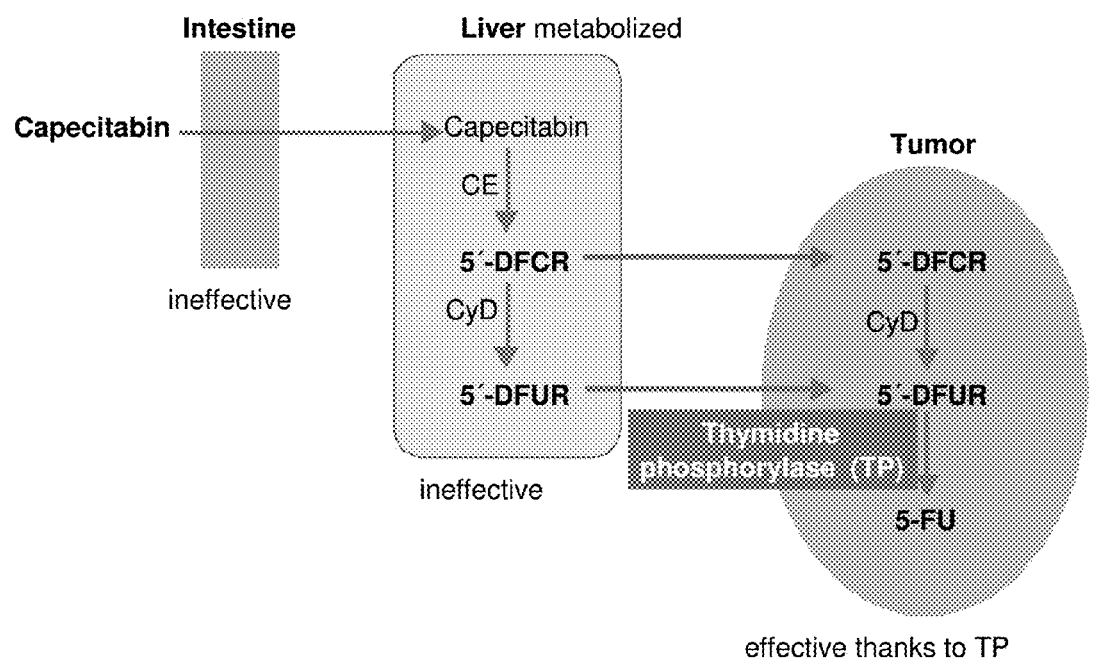

METHOD FOR ESTABLISHING THE SENSITIVITY OF TUMOURS TO CAPECITABIN AND TEST KIT

CROSS-REFERENCE TO RELATED APPLICATIONS

This application is the United States National Stage filing under 35 U.S.C. §371 of International Application No. PCT/DE2007/001369, filed on Aug. 1, 2007, and claiming priority to German Application No. 10 2006 037 158.5, filed on Aug. 2, 2006. Both of the foregoing are incorporated by reference herein.

BACKGROUND OF THE INVENTION

1. Field of the Invention

The invention relates to a method to identify a human tumor which is insensitive or sensitive with a view to an administration of capecitabine, if applicable in combination with Docetaxel or Paclitaxel or the humanized antibody Herceptin® (Herceptin® is a registered trademark of Genentech, Inc., for pharmaceutical preparations for the treatment of cancer) or COX-2 inhibitors or VEGF inhibitors, preferably to identify the insensitivity or sensitivity of a metastatic carcinoma of the large intestine or the breast or another solid tumor, as well as a test kit for the determination of such an insensitivity or sensitivity. Fields of application of the invention are the pharmaceutical industry and bio-sciences: biology, biochemistry, biotechnology, medicine and medicinal technology.

2. Background of the Art

The treatment of metastatic tumors is a great challenge for oncologists. For example, 30-40% of all patients with breast cancer in western countries develop a metastatic mamma carcinoma.

Capecitabine (IUPAC name: Pentyl[1-(3,4-dihydroxy-5-methyl-tetrahydrofuran-2-yl)-5-fluoro-2-oxo-1H-pyrimidin-4-yl]aminomethanoat) is a chemotherapeutic which is regularly used in the treatment of tumors of the breast and the intestines or other solid metastatic tumors.

Capecitabine is converted in the body, finally preferably in the tumor, to form the compound 5-Fluorouracil (5-FU). In cell division, 5-FU is integrated into the DNA instead of Cytosin and Thymin as a result of its structural similarity with them. The DNA formed in this context is not functional.
Fluoropyrimidine in Therapy of a Metastatic Mamma Carcinoma In 1987, Hansen reported for the first time on the use of a therapy with continuous administration of low-dose 5-FU in patients with highly intensive previous treatment with progressive mamma carcinoma (Hansen et al., 1987). Of 25 patients, 8 achieved an objective reaction. Toxicities such as hand and foot syndrome, mucositis, diarrhea were remedied by a short-term interruption of the therapy or a reduction of the dose. These results were repeatedly confirmed by Jabboury 1989, Huan 1989 and by Hansen 1991.

However, long-term infusions are technically complicated, expensive, work-intensive and above all uncomfortable for patients and additionally strained by complications of the central nervous catheter. Oral administration of a fluoropyrimidine on the other hand means an elegant method of imitating the effective mechanism of the protracted or 5-FU long-term infusion.

Capecitabine is an oral fluorpyrimidine carbamate. Capecitabine itself does not have a cytotoxic effect, but is converted by three enzymatic steps, mainly in the tumor, to form the active cytotoxic metabolite Fluorouracil (5-FU). Fluorouracil belongs to the group of the antimetabolites, as a pyrimidine antagonist it competes with the actual substrate and leads to an inhibition of the nucleic acid synthesis. Integration of 5-FU instead of Uracil leads to an inhibition of the RNA and protein synthesis. As a result of a blockade of the methylization of desoxyuridylic acid, there is formation of thymidylic acid, as a result of which the synthesis of the DNA is additionally influenced. The effect of the DNA and RNA deprivation most strongly affects the cells which proliferate more quickly and metabolize capecitabine more quickly to form 5-FU.

After oral absorption, capecitabine is firstly metabolized to 5'-desoxy-5-fluorcytidin (5'DFCR) with the help of hepatic carboxylesterases, the former being converted into 5'-desoxy-5-fluoruridin (5'-DFUR) by cytidin desaminase, which is mainly located in the liver and the tumor tissue (FIG. 1). Thereafter, 5'DFUR is catalytically activated with the help of the thymidine phosphorylase (TP), mainly in the tumor (Ishitsuka et al., 1995). Thymidine phosphorylase, also under the name "Tumor Associated Angiogenesis Factor", mainly exists in high concentrations in malign cells. Matching its expression in the tumor, a tumoral and a peritumoral fraction can be distinguished. The peritumoral fraction induces the formation of VEGF (Vascular Endothelial Growth Factor) in the healthy cells surrounding the tumor (Nicholas S. Brown et al.: Thymidine Phosphorylase Induces Carcinoma Cell Oxidative Stress and Promotes Secretion of Angiogenic Factors. Cancer Research 60 (2000) 6298-6302), which for its part leads to an increased formation of new vessels in the area of the tumor. Accordingly, the TP correlates with fast malignoma growth, aggressive invasion behavior and a bad forecast (Folkman et al., 1996). This is why precisely such patients with a bad forecast should profit from therapy with capecitabine.

Capecitabine has an additive effect with other cytotoxic substances. Examinations were able to show additive effects with CPT-11, Tomudex™ (Tomudex™ was previously a registered trademark of Imperial Chemical Industries PLC), Mitomycin C or Cyclophosphamide and supra-additive ones with Paclitaxel or Docetaxel. Synergetic effects exist between capecitabine and a radiation therapy. These effects were not observed under 5-FU and are to be put down to the up-regulation of the key enzyme in the capecitabine metabolism as a result of the aforementioned cytostatics, but also the radiation (Sawada et al., 1998, 1999).

The drug capecitabine (brand name: Xeloda® (Xeloda® is a registered trademark of Hoffman-LaRoche Inc. for a pharmaceutical preparation, namely, an anticancer drug)) was registered in 2001 for therapy of a metastatic carcinoma of the large intestine. The year after, the drug was registered in combination with administration of Docetaxel (Taxotere® (Taxotere® is a registered trademark of Aventis Pharma S.A. for pharmaceutical preparations, namely, an anti-cancer preparation) for treatment of a metastatic mamma carcinoma. This was based on a clinical Phase III study, in which capecitabine was checked alone against Docetaxel in combination with Docetaxel (Taxotere®). For the first time, a significant extension of life for patients with metastatic breast cancer was achieved in this study. Although the effect of capecitabine as a so-called pro-drug chemotherapeutic is automatically bound to the existence of the enzyme thymidine phosphorylase, registration was granted without downstream proof. This also applies to all other fields of indication of capecitabine.

Results of Clinical Studies

Capecitabine was tested as a first, second and third line therapy in clinical studies on metastatic mamma carcinomas.

In a Phase II study (Blum et al., 1998), 162 patients with massive previous treatment and metastatic mamma carcinomas were given capecitabine in a dose of 2510 mg/m²/day for 14 days, followed by a 7-day therapy break. The treatment was continued in 3-week cycles.

The duration of the therapy was based on the sequence. Patients who reacted to the therapy with capecitabine were further treated until the tumor progress. An inclusion criterion was a primary or secondary resistance or a therapy failure in chemotherapy with Paclitaxel, 90% did not react to Anthracycline, 82% did not react to a therapy regime containing 5-FU.

46% had at least 2 or 3 previous therapies, 85 patients (53%) an adjuvant previous therapy with 5-FU. 89% of the patients treated had already received four or more cytotoxic substances.

An objective remission rate of 20% was observed in the "intend to treat" evaluation (162 patients) and confirmed by an independent commission. Three complete remissions observed lasted for 106, 109 and 194+ days.

43% of the patients profited thanks to a stable sequence of the illness. In a sub-group analysis, 42 of the anthracycline and paclitaxel therapy refractory patients again showed a reaction rate of 29%.

The mean remission duration was 241 days, the median time until progression 93 days and the median survival of 384 days was surprisingly long for these patients with intensive previous treatments.

Not only the anti-tumorous potency, but in particular the palliative effect, which is important for this group of patients with a view to pain reduction, was proven by the study for capecitabine. Of 51 patients who documented a pain figure above 20 mm at the start on the study on an analogue pain scale, the pain was reduced by more than 50% by the therapy in 47% of them.

The capecitabine therapy showed an excellent tolerability profile. No pre-medication or primary prophylaxis were necessary. Therapy-induced fatalities did not occur.

In a further phase II study, capecitabine was used in the second line in patients after anthracycline failure in comparison with Paclitaxel. 36% of the patients with capecitabine achieved an ORR, 21% overall response being achieved by Paclitaxel (O'Reilly et al., 1998). The study was ended prematurely after recruiting of 44 patients, as many patients had clear preferences with a view to their medication, either preferring Paclitaxel or an oral substance. Randomization was therefore difficult.

Under capecitabine and under Paclitaxel, a median reaction duration of 9.4 months was established. The median time until tumor progression was 3.0 months (92.5 days) for capecitabine and 3.1 months (95 days) for Paclitaxel.

Current data of a phase II study concluded with recruiting by Reichardt et al. on effectivity and tolerability of a capecitabine therapy of a metastatic mamma carcinoma following a previous therapy containing taxane were presented at the San Antonio Breast Cancer Symposium 2000. Up to now, 97 patients included in the study have been evaluable. Median age 55 years (range 36-77), median Karnofsky index 90% (range 60-100). 91% of the patients had previous therapy containing anthracycline, 100% containing taxane (51% Paclitaxel, 45% Docetaxel, 4% both taxanes).

Capecitabine was administered in a dose of 1250 mg/m² twice a day, morning and evening, for 14 days followed by a 7-day break.

After an average of 4 cycles (range 1-15), 77 and 68 patients are evaluable for toxicity and effectivity respectively. Toxicity is mild with 40% hand and foot syndrome, nausea and vomiting 38%, diarrhea 21% and lethargy 18% CTC degree 1 and 2. Merely 14% developed a degree 3 hand and foot toxicity.

2 patients (3%) achieved a complete remission, 15 (22%) a partial one and 47% showed stabilization of the disease. All told, tumor control was achieved in 72% of the patients with intensive previous treatment (Reichardt et al, 2000).

In accordance with a phase III study (O'Shaughnessy J et al. Superior survival with capecitabine plus docetaxel combination therapy in anthracycline-pretreated patients with advanced breast cancer: phase III trial results. J Clin Oncol 20 2812-23 (2002), a distinct increase of the effect by combination therapy with capecitabine and Docetaxel compared with Docetaxel was observed in patients with a metastatic mamma carcinoma, but merely 42% of the tumors examined in the combination therapy showed a reaction to the treatment.

The disadvantage of the state of the art is that a high percentage of the patients does not react to the treatment with capecitabine or capecitabine in combination with taxanes. As capecitabine has been admitted without a downstream proof of thymidine phosphorylase, treatment is also given as a rule to insensitive or non-reactive patients with no kind of benefit from the therapy who are unnecessarily subjected to the undesirable effects without a therapeutic success occurring or being expected.

Therapies based on molecular biology are always highly selectively aimed at blocking certain cellular receptors or enzymes of the tumor cells. This is why their good effectivity, but also the low range of undesired effects compared with chemotherapy can be explained. Accordingly, detection of the estrogen and progesterone receptors is absolutely necessary for implementation of an anti-hormonal therapy. This applies in the same way to the implementation of a herceptin therapy. Here, detection of HER-2 by means of immunohistochemistry (ICH) or fluorescence in situ hybridization (FISH) is necessary. The drugs Xeloda® (capecitabine), Celebrex® (celecoxib) (Celebrex® is a trademark of G.D. Searle LLC for pharmaceuticals in the nature of anti-inflammatory analgesics) and Avastin® (bevacizumab), which are also highly selective, were given their registration without downstream detection. Nevertheless, they can only develop their effect if the corresponding target substrate exists in the tumor tissue. This is why it appears necessary to bind the use of the drugs to the detection of the corresponding target substrates as well.

BRIEF SUMMARY OF THE INVENTION

For this reason, a method for the individual establishment of the effectivity of capecitabine or its metabolites formed in the body, if applicable in combination with Docetaxel or Paclitaxel and/or Herceptin® (trastuzumab) and/or COX-2 inhibitors and/or angiogenesis inhibitors, is desirable before the active substance or combination of active substances is administered on patients.

Therefore, the task of the invention is to state a method making identification of the insensitivity or non-reactivity or the sensitivity or reactivity of a human solid tumor with regard to treatment with capecitabine possible and of providing a test kit making simple implementation of the invention.

Therefore, the solution of the tasks forming the invention comprises determination of thymidine phosphorylase (TP) in the tumor tissue and detecting it as a prerequisite for the use of the drug capecitabine.

This finding or effect is supplemented by detection of unexpectedly low concentrations of COX-2 (cyclooxygenase-2) in the tumor tissue, in particular of insensitive patients. This enzyme is the target structure for the drug group of the COX-2 inhibitors, e.g. Celebrex® (Celecoxib, 4-[5-(4-methylphenyl)-3-(trifluoromethyl)pyrazol-1-yl]). Accordingly, the same principle, which provides for purposeful use of the drug in tumor therapy, in particular combined use of capecitabine and COX-2 inhibitors, preferably of capecitabine and Celebrex®, only applies after detection of this enzyme.

Therefore, another solution of the task according to the invention comprises determination of COX-2 in the tumor tissue and detecting it for a reliable use of the drug and, if applicable, of a further active substance.

In particular, the determination both of TP and also of COX-2 in the tumor tissue has quite surprisingly turned out to be a reliable instrument for the prognosis of the insensitivity or sensitivity of human tumors towards capecitabine, particularly in combination with COX-2 inhibitors, preferably with Celebrex®, and/or in combination with Docetaxel or Paclitaxel and/or in combination with Herceptin® (trastuzumab). The same applies accordingly to the determination of VEGF and VEGF receptors for combination with angiogenesis inhibitors, e.g. Avastin®.

Thus, a further solution of the task according to the invention entails determining TP in the tumor tissue and also detecting it as a prerequisite for reliable use of the medication and, if applicable, a further active substance or a number of active substances.

In a further embodiment of the invention, the existence of VEGF and VEGF receptors is detected for the implementation of an angiogenesis inhibitor, e.g. with Avastin®.

Therefore, the invention is principally based on the fact that human thymidine phosphorylase and/or human cyclooxygenase 2 and/or VEGF and VEGF receptors are determined in the tissue of a human tumor, in particular a metastatic carcinoma of the large intestine or the breast or of any other solid, malign tumor, in particular a metastatic one.

As a function of the outcome(s) of this determination, capecitabine is then administered, if applicable in combination with Docetaxel and/or with Paclitaxel and/or with the humanized antibody Herceptin and/or with COX-2 inhibitors, in particular Celebrex® and/or with an angiogenesis inhibitor, preferably Avastin®.

BRIEF DESCRIPTION OF THE FIGURE

FIG. 1 shows the conversion and efficacy of capecitabine in the body.

DETAILED DESCRIPTION OF THE INVENTION

For the method according to the invention, tissue or tissue material isolated from the human tumor, e.g. by means of a biopsy, or tumor material which has already been isolated is preferably used. For the isolation, principally all possible standard methods or other known methods for the isolation of tissue or tissue material from a solid tumor are suitable, for example a resection of tumor material from the patient. Preferably, tissue sections, but also other material obtained from the tissue, for example tissue homogenizate, cells, cell components or solutions containing the same, are preferably suited as tissue.

Particularly preferably, thymidine phosphorylase and/or cyclooxygenase 2 is determined immuno-histologically in the isolated tumor tissue, preferably tissue sections. VEGF and VEGF receptors are equally detected immuno-histologically. In particular, all standard methods of antibody blotting, immuno-blotting and immuno-histochemistry by means of which proteins can be made visible in tissue with the help of antibodies or other specific ligands, in particular by direct methods (use of marked primary antibodies), indirect methods (use of marked secondary antibodies) and/or the avidine-biotin method (use of biotinylized antibodies and marked streptavidin) are suited for this.

Immuno-histological methods for the determination of TP and/or COX-2 and/or VEGF and VEGF receptors, in particular making use of fixed tumor tissue or tissue sections, as the case may be, particularly have the advantage that they are particularly simple and can be implemented directly after the isolation of the tumor tissue.

Another possibility of implementation of the method according to the invention entails cells of tumor liquid or punctuates or similar, which have been attached to a holder, in particular an object holder, by means of centrifugation or other methods, or have grown on a holder by means of a cell culture technique being used immuno-histologically for the determination of TP and/or COX-2 and/or VEGF and VEGF receptors. Preferably, the quantity of anti-TP antibodies and/or anti-COX-2 and/or VEGF and VEGF receptor antibodies is selected so low for the implementation of the method according to the invention by means of immuno-histological methods that a significantly increased quantity or concentration of TP and/or COX-2 and/or VEGF and VEGF receptors in the tissue (just about) causes recognizable signals as a function of the marking and reading apparatus used, e.g. a fluorescence microscope, whereas a normal concentration, one comparable with healthy tissue or lower concentration of TP and/or COX-2 and/or VEGF and VEGF receptors no longer causes recognizable signals, as a result of which implementation of the method according to the invention is simplified even further.

Accordingly, all possible solid-phase based assays (e.g. ELISAs or corresponding blot assays, Western blots, Southern blots, Northern blots, arrays etc.) are suited for detection of TP and/or COX-2 and/or VEGF and VEGF receptors according to the invention.

According to another aspect of the invention, the presence of thymidine phosphorylase and/or cyclooxygenase 2 and/or VEGF and VEGF receptors in the tumor tissue is detected by determination of its biological function, for example by addition and measurement of the implementation of enzyme substrate by TP (e.g. of 5'-DFUR) and/or by COX-2 (e.g. of anandamide) in the tissue or tissue material. Beneficially, a standard with a known quantity of TP and/or COX-2 is measured parallel to this.

But also determination of gene expression of TP and/or COX-2 and/or VEGF and VEGF receptors is suited in order to detect their presence and concentration in the tissue material. For this, in particular, all possible standard methods for the detection of the mRNA of TP and/or COX-2 and/or VEGF and VEGF receptors in the tissue or tissue material are suited. For example, RMA is isolated from the tissue and transcribed into cDNA by means of RT-PCR. The cDNA is subsequently selectively reproduced by a PCR with primer sequences of human TP and/or COX-2 and/or VEGF and VEGF receptors and the PCR products are separated by gel electrophoresis and determined. But use of real-time PCRs is also suited. In particular, the synthesis of cRNA from the cDNA by second strand synthesis, fragmenting of the products and subsequent detection of products specific to TP and/or COX-2 and/or VEGF and VEGF receptors by means of an oliognucelotide array, in particular micro-arrays, is also favorable for the implementation of the method according to the invention.

According to the invention, all methods are preferably suited for, the determination of TP and/or COX-2 and/or VEGF and VEGF receptors in which tumor tissue or parts thereof are put in contact with at least one substance which has been at least partly dissolved, manifesting affinity to the gene of human thymidine phosphorylase and/or to variants and/or to parts thereof and/or to its mRNA and/or to its genetic products and/or cleavage products, polypeptides or peptides derived therefrom, and/or is brought into contact with at least one substance manifesting affinity to the gene of human cyclooxygenase 2 and/or to variants and/or to parts thereof and/or to its mRNA and/or to its genetic products and/or cleavage products, polypeptides or peptides derived therefrom, and/or is brought into contact with at least one substance manifesting affinity to the gene of human VEGF and human VEGF receptor and/or to variants and/or to parts thereof and/or to its mRNA and/or to its genetic products and/or cleavage products, polypeptides or peptides derived therefrom. In this context, the affinity is preferably shown via an association constant of $Ka > 1000\ M^{-1}$, by which a particularly specific detection is made possible.

The enzyme substrate of TP and/or COX-2 containing at least one substance, oligonucleotide sequences of TP and/or COX-2 and/or VEGF and VEGF receptors or complementary sequences thereof, proteins, peptides or structures derived therefrom, in particular monoclonal antibodies and/or polyclonal antibodies and/or antibody fragments aimed against TP and/or COX-2 and/or VEGF and VEGF receptors are particularly preferably used.

In a further embodiment of the invention, at least one substance which has at least been partly dissolved, preferably directly, is connected with a marker, for example an enzyme (e.g. AP or HRP), as a result of which particularly simple detection of TP and/or COX-2 and/or VEGF and VEGF receptors is made possible.

Preferably, the marker is formed as a (fluorescence) dye, contrast agent, radionuclide, biotin, peptide, protein or microparticle or entails the same, particularly preferably being formed as a marked secondary antibody or marked protein A or marked protein G or structure derived therefrom.

The connection between the at least one substance and the marker is preferably formed chemically, electrostatically and/or via hydrophobic interactions, with a covalent connection being particularly suited.

In accordance with the method according to the invention, a human tumor insensitive with regard to administration of capecitabine, particularly insensitive with a view to administration of capecitabine in combination with Docetaxel or Paclitaxel or Herceptin, or insensitive with regard to administration of capecitabine in combination with a COX-2 inhibitor, e.g. Celebrex®, and/or an angiogenesis inhibitor, e.g. Avastin®, is identified by the fact that thymidine phosphorylase and/or cyclooxygenase 2 and/or VEGF and VEGF receptors are essentially not detectable in the tumor tissue examined and/or their gene expression or enzymatic activity is significantly lower and/or not significantly higher (in particular TP) than in comparable healthy tissue.

A human tumor sensitive with a view to capecitabine or sensitive with a view to COX-2 inhibitor or sensitive with a view to an angiogenesis inhibitor, in particular sensitive with a view to capecitabine in combination with Docetaxel or Paclitaxel or Herceptin® or sensitive with a view to capecitabine in combination with a COX-2 inhibitor, preferably celecoxib (Celebrex®) or etoricoxib (Arcoxia®) (Arcoxia® is a trademark of Merck Sharp & Dohme Corp. for anti-inflammatory analgesics and pharmaceutical preparations for the treatment of arthritis), or sensitive with a view to capecitabine in combination with an angiogenesis inhibitor, preferably Avastin®, or sensitive with a view to capecitabine in combination with a COX-2 inhibitor, preferably celecoxib (Celebrex®) or etoricoxib (Arcoxia®) and in combination with an angiogenesis inhibitor, preferably Avastin®, is identified according to the invention by the fact that thymidine phosphorylase and/or cyclooxygenase 2 and/or VEGF and VEGF receptors are detectable in its tumor tissue and/or its gene expression or enzymatic activity is significantly higher than and/or comparable with (in particular COX-2) corresponding healthy tissue.

For example, the following results were obtained in the determination of TP and COX-2 in the tumor tissue:

a) TP and/or COX-2 is not detectable and/or their concentration is significantly lower than in corresponding healthy tissue: The tumor is identified as insensitive with a view to treatment of the patient with capecitabine, if applicable in combination with a further drug.

b) TP and/or COX-2 is detectable and/or the concentration is significantly higher than in corresponding healthy tissue: The tumor is identified as sensitive with a view to treatment with capecitabine, if applicable in combination with a further drug, in particular in combination with a COX-2 inhibitor, preferably Celebrex®.

c) TP and/or COX-2 is detectable and/or the concentration is significantly higher than in corresponding healthy tissue and/or COX-2 is not detectable and/or the concentration is significantly lower than in corresponding healthy tissue. The tumor is identified as sensitive with a view to treatment with capecitabine, if applicable in combination with a further drug, in particular in combination with Docetaxel or Paclitaxel or Herceptin®.

d) TP is detectable and/or its concentration is significantly higher than in corresponding healthy tissue and/or COX-2 is detectable and/or its concentration is comparable with corresponding healthy tissue: The tumor is identified as sensitive with a view to treatment with capecitabine, if applicable in combination with a further drug, in particular in combination with a COX-2 inhibitor, preferably Celebrex®.

e) TP is not detectable and/or its concentration is significantly lower than in corresponding healthy tissue and/or its concentration is comparable with corresponding healthy tissue and/or COX-2 is detectable and/or its concentration is comparable with corresponding healthy tissue and/or its concentration is significantly higher than in corresponding healthy tissue: The tumor is identified as insensitive with a view to treatment with capecitabine, if applicable in combination with a further drug, in particular in combination with a COX-2 inhibitor, preferably Celebrex®.

A further aspect of the invention relates to a test kit for identification of a human tumor, in particular a metastatic carcinoma of the large intestine or the breast or another solid metastatic tumor, which is insensitive or sensitive with a view to administration of capecitabine, if applicable in combination with Docetaxel or Paclitaxel or Herceptin® or an COX-2 inhibitor, in particular Celebrex® or an angiogenesis inhibitor, in particular Avastin®. The test kit contains at least one at least partly soluble or dissolved substance manifesting affinity to the gene of human thymidine phosphorylase and/or to variants and/or to parts thereof and/or to its mRNA and/or to its genetic products and/or cleavage products, polypeptides or peptides derived therefrom and/or the test kit contains at least one at least partly soluble or dissolved substance manifesting affinity to the gene of human cyclooxygenase 2 and/or to variants and/or to parts thereof and/or to its mRNA and/or to its genetic products and/or cleavage products, polypeptides or peptides derived therefrom, and/or the test kit contains at least one at least partly soluble or dissolved substance manifesting affinity to the gene of human VEGF and/or VEGF receptors and/or to variants and/or to parts thereof and/or to its mRNA and/or to its genetic products and/or cleavage products, polypeptides or peptides derived therefrom. An enzyme substrate of TP and/or an enzyme substrate of COX-2, oligonucleotide sequences of TP and/or COX-2 and/or VEGF and VEGF receptors or complementary sequences thereof, proteins, peptides or structures derived therefrom, in particular monoclonal antibodies and/or polyclonal antibodies and/or antibody fragments aimed against TP and/or COX-2 and/or VEGF and VEGF receptors, are particularly suitable. A particularly preferred version of the test kit according to the invention contains a suitable quantity of antibodies, in particular monoclonal antibodies, against TP and/or COX-2, and, if applicable, fluid to dissolve the antibodies, washing buffer, marked secondary antibodies or marked protein A or protein G or fragments thereof, and other materials, instructions for the use of the test kit and a packaging. Particularly preferably, the test kit contains primary antibodies marked with a fluorescence dye or with an enzyme against TP and/or COX-2 and/or VEGF and VEGF receptors.

Another aspect resulting from the outcome of the work on the invention relates to the use of capecitabine and COX-2 inhibitors, preferably capecitabine and Celebrex® and angiogenesis inhibitors, preferably Avastin®, for the manufacture of a drug against a human tumor, in particular against a metastatic carcinoma of the large intestine or the breast or another, in particular metastatic, solid tumor. The drug is preferably suited for the therapy of patients if TP and/or COX-2 and/or VEGF and VEGF receptors have been determined and established beforehand in the tissue of the tumor to be treated.

For the first time, the invention enables a forecast of the treatment success for patients with solid tumors, in particular against a metastatic carcinoma of the large intestine or the breast or another, in particular metastatic, solid tumor, compared with a treatment with capecitabine, in particular in combination with Docetaxel or Paclitaxel or Herceptin® or a COX-2 inhibitor, preferably Celebrex®, and/or in combination with angiogenesis inhibitors, preferably Avastin®. Use of these drugs is bound to detection of the corresponding target substrates, in order to increase the effectivity of these therapies distinctly.

The possibilities for the production of an onco-biogram are distinctly extended by the invention by means of application of many different targets. In this context, above all tumor properties which are the target for new therapies or markers permitting precise statements about the malignity of the tumor tissue are determined. This opens up treatment changes above all for the patients in whom all the established therapies have failed.

Patients who are insensitive to such a treatment do not suffer the undesired effects of this medication treatment as a result of the identification according to the invention and there is no longer any need to wait for the failed attempt at treatment before further measures for maintaining life can be taken.

Further beneficial properties of the invention also become visible from the following examples and explanations.

It was a total surprise that the examinations leading to the invention showed that the immuno-histological detection of thymidine phosphorylase in the tumor tissue is causally connected with a distinct reduction of the TTP (time to progression). Patients without expression of the enzyme, on the other hand, have no benefit from the therapy.

In a prospective phase II study held within the work concerned with the invention, the effect of the drug combination capecitabine/trastuzumab on a metastatic mamma carcinoma was examined. Both drugs are highly target-orientated therapeutics. For its effectivity, capecitabine needs TP and trastuzumab HER-2 (Human Epidermal growth Factor Receptor 2). Inclusion criteria were progression of the disease after conclusion of chemotherapies containing anthracycline and taxane and the detection of HER-2, but not of TP. After an observation period of 34 months, 4 (17%) of 27 patients had a complete remission of the disease, 8 (35%) a partial remission, 9 (39%) a stable disease. With 2 (9%), the disease progressed without reduction. (Schaller G et al.: Phase II Study of capecitabine Plus Trastuzumab in Human Epidermal Growth Factor Receptor 2-Overexpressing Metastatic Breast Cancer Pretreated With Anthracyclines or Taxanes. J Clin Oncol. (2007) Jun. 18).

The conspicuous thing in this study was that an unusually long-lasting and stable complete remission occurred in four patients, which was extremely surprising with the extremely unfavorable starting situation.

The hypothesis was formulated that the good reaction could be connected with the TP expression in the tumor. As a result, TP was retrospectively established by immuno-histology intratumorally, peritumorally and as a total fraction together with COX-2, VEGF and K18 (Keratin 18) in the study patients. These parameters were then subjected to an analysis with the help of mathematical logic (Klaus Truemper: Design of Logic-based Intelligent Systems, published by John Wiley & Sons 2004) together with 30 further biological, therapeutic and anamnetic data. For organizational reasons, only 14 samples were available for the analysis. The essential outcome was that the combination of factors of strong expression figures for TP and low ones for COX-2 was decisive for a long TTP.

This outcome is explained in more detail on the basis of two patients' sequences:

Patient 1 is now 48 years old. In 1995, the operative primary therapy in the form of an Ablatio mammae right was carried out. Histologically, this was a pT2 (ø 2.8 cm), pN1 (2/18 Lk attacked), pMx ductal mamma carcinoma, G2. The operation was followed by an adjuvant chemotherapy with CMF, in 1997 the first breast wall relapse occurred, being removed operatively. There followed local radiation. In 1999 a further breast wall relapse was removed operatively. In the same year, bone metastases occurred for the first time (left hip, Os occipitale incl. soft tissue) and skin metastases (right supraclavicular and diffuse, right thoracic wall). There was the first administration of trastuzumab (Herceptin®) in combination with various anti-hormonal therapies (Tamoxifen, aromatase inhibitors, GnRH analogs, ovarectomy). In December 2003, capecitabine (Xeloda®) was used in combination with trastuzumab for the first time, being permanently taken until now. The bone metastases were radiated. With this treatment, a complete remission was achieved, lasting for almost three years up to now. On Apr. 9, 2006, an onco-biogram was produced. In this context, a strong expression of thymidine phosphorylase was seen both in the tumor (IRS 9) and also peritumoral (IRS 9) and low figures for the COX-2 (IRS 2). The patient is very well. She is working in her profession as a hairdresser and has just returned from a three-week trip to Thailand.

Patient 2 is now 69 years old. In 1999, the primary therapy was held in the form of a part mastectomy with axillary dissection. This was a multifocal ductal mamma carcinoma, pT2, pN 1 biii (7/15), G3, DCIS G2 (30%). It was followed by an adjuvant chemotherapy with 4×EC, radiation of the remaining breast followed by 4× Taxol. The tumor expressed the estrogen receptor. This is why there was treatment with Tamoxifen from October 1999 until September 2001. In August 2001, a solitary liver metastasis ø 3 cm was detected by sonography and NMRI. The HER-2 determination done at this time resulted in an over-expression of 3+. The patient was included in the capecitabine/trastuzumab study, under which there was a complete remission, lasting until the present. Retrospective determination of TP and COX-2 resulted in a distinct expression for TP in the tumor (IRS 6) and also, particularly, peritumoral (IRS 9) and a weak expression (IRS 2) of COX-2. The patient is well. She has just built a new house together with her husband.

All the features stated in the above description, the following claims and the illustrations can be of significance for the implementation of the invention in its various embodiments both individually and also in arbitrary combinations.

The invention claimed is:

1. A method for treating a human tumor in a patient, comprising determining the sensitivity of said human tumor to a combination of capecitabine, a COX-2 inhibitor, and an angiogenesis inhibitor, comprised of the following steps:
   (a) obtaining a tumor tissue sample from said human tumor;
   (b) testing said tumor tissue sample to determine a first amount of a group of indicators including thymidine phosphorylase, vascular endothelial growth factor (VEGF), vascular endothelial growth factor-receptor (VEGF-R), and cyclooxygenase 2, wherein the thymidine phosphorylase is detected from a peritumoral fraction of said tumor tissue sample;
   (c) comparing the first amount of each of said group of indicators to a second amount of said group of indicators, wherein said second amount of said group of indicators is obtained from a non-tumor tissue sample; and
   (d) determining the sensitivity of said human tumor to capecitabine in combination with the COX-2 inhibitor and the angiogenesis inhibitor, wherein when the first amount is greater than the second amount, the test is indicative of sensitivity, and wherein when the first amount is less than the second amount, the test is indicative of insensitivity; and,
   (e) when the test is indicative of sensitivity, administering to said patient harboring the human tumor capecitabine in combination with the COX-2 inhibitor and the angiogenesis inhibitor.

2. The method of claim 1 wherein the presence of at least one indicator selected from the group consisting of thymidine phosphorylase in the peritumoral fraction, vascular endothelial growth factor (VEGF), vascular endothelial growth factor-receptor (VEGF-R) and cyclooxygenase 2 is determined from the tumor tissue sample by immunohistology.

3. The method of claim 1 wherein the tumor tissue sample is brought into contact with at least one substance manifesting affinity to at least one member of the group consisting of the gene of human thymidine phosphorylase, mRNA of human thymidine phosphorylase, the gene of human cyclooxygenase 2, and the mRNA of human cyclooxygenase 2.

4. The method of claim 3, wherein the affinity is shown via an association constant of $Ka > 1000\ M^{-1}$.

5. The method of claim 3 wherein the at least one substance is connected with a marker.

6. The method of claim 5 wherein said marker has been formed from at least one member of the group consisting of a dye, a contrast agent, a radionuclide, a biotin, a peptide, a protein, and a microparticle.

7. The method of claim 5 wherein said marker has been formed from at least one member of the group consisting of a marked secondary antibody, a protein A, a protein G, and a structure derived therefrom.

8. The method of claim 5 wherein said marker is connected with the at least one substance by at least one member of the group consisting of a chemical interaction, an electrostatic interaction, and a hydrophobic interaction.

9. The method of claim 8 wherein the connection between the at least one substance and the marker is covalent.

10. The method of claim 1 wherein the presence of thymidine phosphorylase in the peritumoral fraction is determined from the tumor tissue sample by immunohistology, and wherein at least one indicator selected from the group consisting of vascular endothelial growth factor (VEGF), vascular endothelial growth factor-receptor (VEGF-R) and cyclooxygenase 2 is determined from the tumor tissue sample by immunohistology.

11. The method of claim 1 wherein the presence of thymidine phosphorylase in the peritumoral fraction is determined from the tumor tissue sample by immunohistology, and wherein at least two indicators selected from the group consisting of vascular endothelial growth factor (VEGF), vascular endothelial growth factor-receptor (VEGF-R) and cyclooxygenase 2 are determined from the tumor tissue sample by immunohistology.

12. A method for treating a human tumor in a patient, comprising determining the sensitivity of said human tumor to a combination of capecitabine, and a COX-2 inhibitor, comprised of the following steps:
   (a) obtaining a tumor tissue sample from a said human tumor;
   (b) testing said tumor tissue sample to determine a first amount of thymidine phosphorylase and a first amount of cyclooxygenase 2; wherein the thymidine phosphorylase is detected from a peritumoral fraction of said tumor tissue sample;
   (c) comparing the first amount of thymidine phosphorylase to a second amount of thymidine phosphorylase and the first amount of cyclooxygenase 2 to a second amount of cyclooxygenase 2, wherein said second amounts are obtained from a non-tumor tissue sample;
   (d) determining the sensitivity of said human tumor to capecitabine in combination with the COX-2 inhibitor, wherein when the first amount of thymidine phosphorylase is greater than the second amount of thymidine phosphorylase and when the first amount of cyclooxygenase 2 is comparable to the second amount of cyclooxygenase 2 or greater, the test is indicative of sensitivity, and wherein when the first amount of thymidine phosphorylase is not greater than the second amount of thymidine phosphorylase or when the first amount of cyclooxygenase 2 is less than the second amount of cyclooxygenase 2, the test is indicative of insensitivity; and,
   (e) when the test is indicative of sensitivity, administering to said patient harboring the human tumor capecitabine in combination with the COX-2 inhibitor.

13. The method of claim 12, wherein the test is indicative of sensitivity when the first amount of thymidine phosphorylase is greater than the second amount of thymidine phosphorylase and when the first amount of cyclooxygenase 2 is greater than the second amount of cyclooxygenase 2.

14. The method of claim 12, wherein the test is indicative of insensitivity when the first amount of thymidine phosphorylase is not greater than the second amount of thymidine phosphorylase or when the first amount of cyclooxygenase 2 is not greater than the second amount of cyclooxygenase 2.

15. The method of claim 12, wherein the test is indicative of insensitivity when the first amount of thymidine phosphorylase is less than the second amount of thymidine phosphorylase or when the first amount of cyclooxygenase 2 is less than the second amount of cyclooxygenase 2.

* * * * *